United States Patent

Carchidi et al.

[11] Patent Number: 6,068,632
[45] Date of Patent: May 30, 2000

[54] BONE TAP APPARATUS

[76] Inventors: Joseph Edward Carchidi, 132 Samuel Ave., West Bridgewater, Mass. 02379; Alan R. Balfour, 1108 Whippoorwill Ct., Petaluma, Calif. 94954

[21] Appl. No.: 09/307,631

[22] Filed: May 7, 1999

Related U.S. Application Data

[60] Provisional application No. 60/085,219, May 12, 1998.
[51] Int. Cl.[7] .................................................. A61B 17/00
[52] U.S. Cl. ............................................. 606/79; 433/165
[58] Field of Search .................. 606/79, 80, 84; 433/165, 141, 144, 221, 225

[56] References Cited

U.S. PATENT DOCUMENTS

| | | | |
|---|---|---|---|
| 4,365,958 | 12/1982 | Vlock | 433/225 |
| 4,871,313 | 10/1989 | Maillefer | 433/225 |
| 4,978,350 | 12/1990 | Wagenknecht | 606/72 |
| 5,643,269 | 7/1997 | Harle | 606/79 |

*Primary Examiner*—Jeffrey A. Smith
*Attorney, Agent, or Firm*—John A. Haug

[57] ABSTRACT

A helical threaded bone tap (10,10',10") for preparing a surgical osteotomy with a defined thread configuration to allow for the insertion of a screw design implant. Incorporated into the tap are four cutting flutes (22) equally spaced, radially, to each other which allow for the removal of bone chips formed during the cutting of the thread. To better assist in this process, cutting flutes (22) are formed with a helical twist to draw the chips outward as the as the osteotomy is being tapped. Distal to the helical threaded bone tap (18) is a driving head having a polygonal configuration (26) and/or a latch type configuration (32) to allow these taps to be driven, respectively, by hand with a ratchet or by using a surgical drilling unit.

5 Claims, 1 Drawing Sheet

BONE TAP APPARATUS

RELATED APPLICATIONS

Benefit is claimed of U.S. Provisional Application 60/085,219, filed May 12, 1998.

FIELD OF THE INVENTION

This invention relates generally to surgical devices used to prepare an osteotomy with a defined geometry to receive a corresponding implant, such as a dental implant, and more particularly, to a helical fluted bone tap.

BACKGROUND OF THE INVENTION

The present invention addresses problems associated with preparing an osteotomy using a bone tap. Presently, a variety of bone preparation tools exist to create the osteotomy to receive an implant. Specifically, when a screw type implant is used and the quality of bone is dense, a surgical bone tap is used for its preparation. Conventional taps have straight, multiple cutting flutes which are used to remove the chips formed during the tapping procedure. However, as these taps are driven down into the osteotomy, they are resisted by the bone chips that are being formed. In fact, the further down the tap goes to prepare the osteotomy, the greater the requirements to increase the applied driving force, as bone chips begin building and backing up resisting the advancing bone tap. When this happens, the user is required to back off the tap and clean the bed of chips formed. If the user does not perform this clearing operation, the tap will either jam in its driver unit, fracture, or strip the threads of the osteotomy site.

SUMMARY OF THE INVENTION

It is an object of the present invention to provide an improved bone tap for surgically preparing an osteotomy for a screw type implant. Another object of the invention is to provide a bone tap with sharp cutting flutes that cut and form the thread configuration in the osteotomy necessary to insert a threaded screw formed implant. Yet another object of the invention is to provide apparatus which will allow a physician to form a threaded osteotomy using a bone tap while minimizing the need to clean its cutting flutes or apply excessive driving force. Still another object of the invention is to provide apparatus to drive such bone taps into an osteotomy using a defined driving geometry to allow these taps to be driven by hand with a ratchet or by using a surgical drilling unit. These and other objects and advantages of the invention will be apparent from the following description taken with reference to the accompanying drawings.

Briefly stated, in accordance with the invention, a bone tap incorporates a defined thread tap geometry with radially spaced helical cutting flutes. Distal to the tip of the tap is a driver head to allow the tap to be driven by hand with a ratchet or by using a surgical drilling unit. The invention solves the problems of a tap jamming in its driver unit, fracturing or stripping the threaded osteotomy site as the helical cutting flutes draw out the formed bone chips decreasing the required driving force needed for tapping a hole. The invention allows a physician to easily form a threaded tapped hole in preparation to receive a screw type unplant while minimizing the risk of certain undesired surgical conditions.

DETAILED DESCRIPTION OF THE PREFERRED EMBODIMENTS

Figure 1:
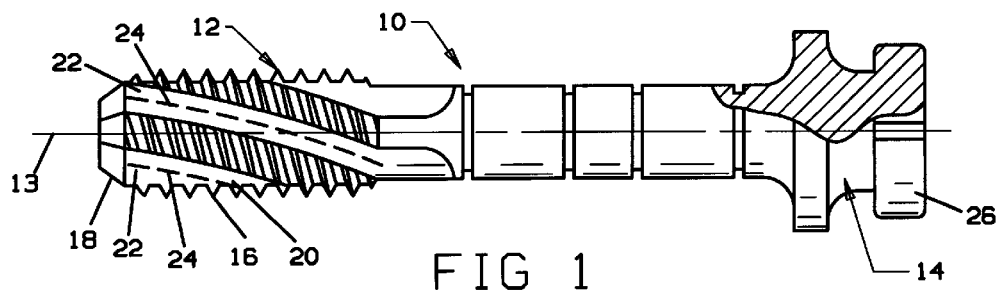
FIG. 1 is a front elevational view, partly in cross section, of a helical threaded bone tap made in accordance with the invention.
Figure 1A:
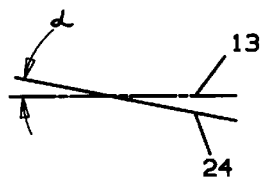
FIG. 1a is schematic view of the longitudinal axes of the FIG. 1 tap and flutes of the tap.
Figure 2:
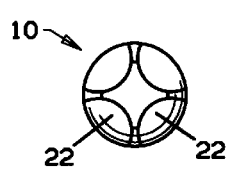
FIG. 2 is a left side elevational view of the FIG. 1 tap.
Figure 3:
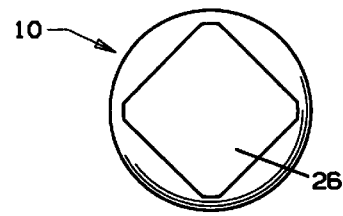
FIG. 3 is a right side elevational view of the FIG. 1 tap.

With reference to FIGS. 1–3, the helical threaded bone tap 10, made in accordance with a first embodiment of the invention, comprises a generally cylindrical threaded shaft body portion 12 and a polygonal driving head 14. Threaded shaft body portion 12 has been designed to locate, tap and prepare a thread geometry for the insertion of a matching screw thread implant. To achieve this goal, the threaded shaft body portion 12 incorporates it lead-in frusto-conical tip 18 and a selected thread geometry 16 with sharp cutting surfaces 20. Cutting surfaces 20 are formed from the radially spaced flutes 22 which extend axially along the threaded shaft body portion 12 intersecting the threads and which extend radially further into the shaft body portion than the threads with the cutting surfaces and the circumferential surface of the shaft body portion forming an acute angle. As the tap is used, the bone chips that are formed during the cutting of the thread are expelled out of the osteotomy site through these radially spaced cutting flutes 22. To improve the efficiency of the release of the bone chips and improve the tap's function, the radially spaced cutting flutes 22 have been formed into a twist or helix having a pitch less than that of the threads with the direction of the longitudinal axis 24 of the flutes forming an angle alpha with the direction of the longitudinal axes 13 of shaft body portion 12 (see FIG. 1a) with alpha being in the range of approximately 10 degrees to 30 degrees. The helical cutting flutes also serve to drive and self tap the bone tap in a direction into the osteotomy.

Figure 4:
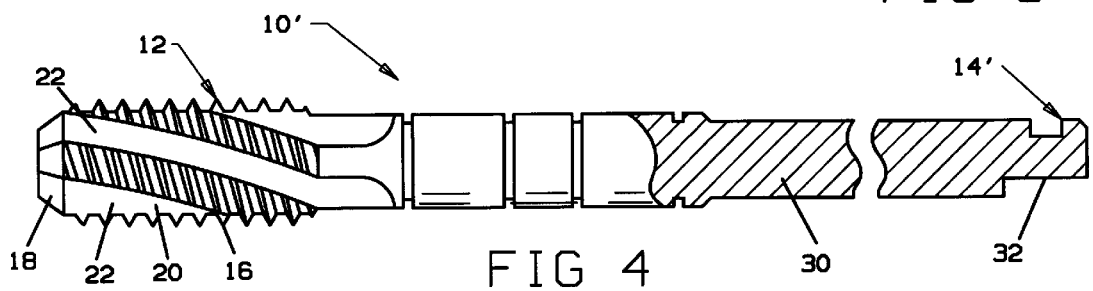
FIG. 4 is a front elevational view, similar to FIG. 1, of a modification of the FIG. 1 tap.
Figure 5:
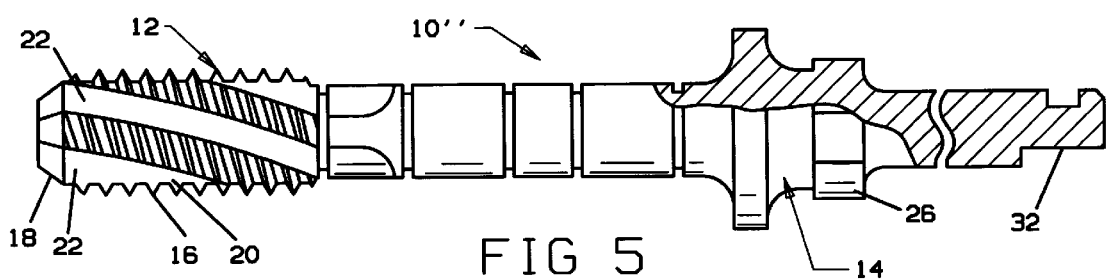
FIG. 5 is a front elevational view, similar to FIG. 1, of another modification of the FIG. 1 tap.
Figure 6:
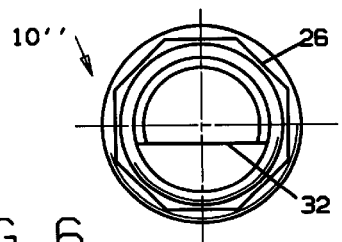
FIG. 6 is a right side elevational view of the FIG. 5 tap.

The coronal end 14 of the helical threaded bone tap 10 incorporates a polygonal driver head 26 which can be driven by a matching female hand driver ratchet. Similarly, as shown in FIG. 4, a helical threaded bone tap 10' has the same threaded shaft body portion 12 but incorporates a straight shaft body 30 and latch type head 32 at coronal end 14' for driving the tool with a surgical drilling unit. FIGS. 5 and 6 show a helical threaded bone tap 10" in which the polygonal drive 26 and latch type head 32 are combined in the same tap to permit driving either by hand or power, as desired.

Thus it will be seen that the helical cutting flutes draw chips formed in the tap in an outward direction in the same manner as a twist drill pulling its formed chips out of a drilled hole. Additionally, the helical cutting flutes serve to drive and self tap the bone tap in an inward direction, i.e., into the osteotomy. It should be understood that this invention includes all modifications and equivalents of the described embodiment falling within the scope of the appended claims.

What is claimed:

1. Bone tap apparatus for use in threading an osteomoty to receive a threaded implant comprising an elongated, generally cylindrical solid body having a longitudinal axis and having an outer surface and having first and second ends, the first end having a portion formed with a lead-in tip and threads having a selected pitch extending along a selected axial length of the body, at least two axially extending recessed flute surface portions extending along the same selected axial length through and radially inwardly beyond the threads, the flute surface portions extending in a direction toward the second end along the longitudinal axis beyond the selected axial length having the threads, the recessed flute surface portions and the outer surface of the body meeting at an acute angle to form a cutting edge, the recessed flute surface portions having a longitudinal axis extending along the selected axial length in a helical path having a pitch less than that of the selected pitch.

2. Bone tap apparatus according to claim 1 in which four recessed flute surfaces are formed in the body radially spaced equally around the circumference of the body.

3. Bone tap apparatus according to claim 1 in which the body has a second end formed with a polygonal driving head.

4. Bone tap apparatus according to claim 1 in which the body has a second end formed with a power driving latch surface.

5. Bone tap apparatus according to claim 1 in which the direction of the longitudinal axis of the cylindrical body and the direction of the longitudinal axis of the flute surface portion forms an angle within the range of approximately 10 to 30 degrees.

* * * * *